United States Patent
Tao

(10) Patent No.: US 9,655,818 B1
(45) Date of Patent: May 23, 2017

(54) MULTI-FILM DELIVERY SYSTEM FOR MULTI-COMPONENT TEETH WHITENING, DESENSITIZATION AND REMINERALIZATION

(71) Applicant: Bo Tao, Chino, CA (US)

(72) Inventor: Bo Tao, Chino, CA (US)

(73) Assignee: Bo Tao, Chino, CA (US)

( * ) Notice: Subject to any disclaimer, the term of this patent is extended or adjusted under 35 U.S.C. 154(b) by 0 days.

(21) Appl. No.: 15/344,579

(22) Filed: Nov. 6, 2016

(51) Int. Cl.
| | |
|---|---|
| *A61K 8/24* | (2006.01) |
| *A61K 8/02* | (2006.01) |
| *A61Q 11/00* | (2006.01) |
| *A61K 8/81* | (2006.01) |
| *A61K 8/86* | (2006.01) |
| *A61K 8/73* | (2006.01) |
| *A61K 8/19* | (2006.01) |
| *A61K 8/97* | (2017.01) |
| *A61C 19/06* | (2006.01) |

(52) U.S. Cl.
CPC .......... *A61K 8/0204* (2013.01); *A61C 19/066* (2013.01); *A61K 8/19* (2013.01); *A61K 8/24* (2013.01); *A61K 8/73* (2013.01); *A61K 8/8135* (2013.01); *A61K 8/8176* (2013.01); *A61K 8/86* (2013.01); *A61K 8/97* (2013.01); *A61Q 11/00* (2013.01)

(58) Field of Classification Search
USPC ............................................ 424/49, 53, 449
See application file for complete search history.

(56) References Cited

U.S. PATENT DOCUMENTS

| | | | | |
|---|---|---|---|---|
| 6,981,874 B2 * | 1/2006 | Allred | ...................... | A61C 5/00 433/215 |
| 2003/0194382 A1 * | 10/2003 | Chang | .................. | A61K 8/0208 424/53 |
| 2004/0219190 A1 * | 11/2004 | Kosti | ................... | A61K 8/0208 424/449 |
| 2005/0276760 A1 * | 12/2005 | Lokken | ................ | A61C 19/063 424/53 |
| 2009/0317339 A1 * | 12/2009 | Sharma | ................ | A61K 8/0237 424/49 |

* cited by examiner

*Primary Examiner* — Walter Webb

(57) ABSTRACT

A multi-film delivery system for a multi-component tooth whitening, desensitization and remineralization composition is disclosed which comprises a first orally dissolvable film made of a liquid-soluble or liquid dispersible polymer system containing a peroxide activation compound or complex and desensitizing agents and/or remineralizing agents and/or anti-inflammatory agents, and a separate second undissolvable film containing a tooth whitening peroxide compound, such as hydrogen peroxide or carbamide peroxide, stabilizers and thickeners, and/or desensitizing agents and/or remineralizing agents and/or anti-inflammatory agents, which, when applied together on teeth surfaces, the peroxide activation compound/complex on the first film activates the peroxide compound on the second film, and accelerates the release of active bleaching radicals for accelerated whitening action. The first and second films are maintained separate from one another until application. The first orally dissolvable film is placed on a surface of the tooth, then immediately hydrates thereby becoming gelatinous upon contact with saliva, and initiates its adhesiveness, the second undissolvable film is then placed on top of the first orally dissolvable film, the peroxide activation compound/complex on the first film reacts with the tooth whitening peroxygen compound on the second film and accelerates the release of active bleaching radicals for rapid whitening action. The dissolution of the first dissolvable film is controlled by interaction with the fluid or liquid contained in the whitening composition on the second undissolvable film.

26 Claims, 8 Drawing Sheets

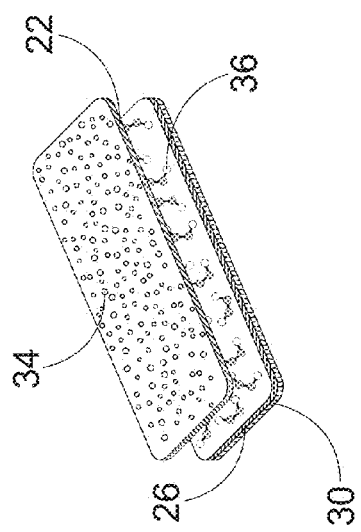
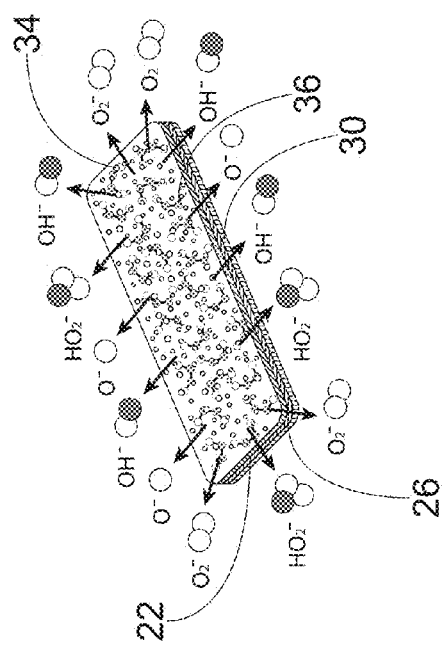
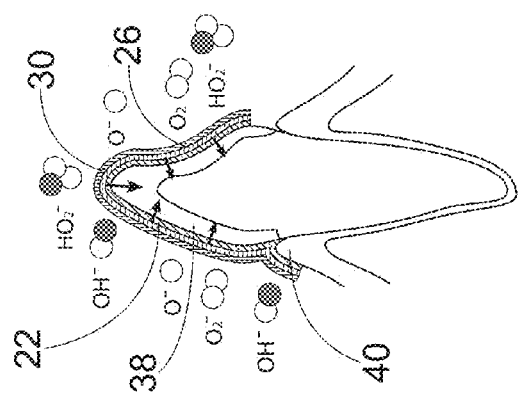
Fig. 19
Fig. 20
Fig. 21

MULTI-FILM DELIVERY SYSTEM FOR MULTI-COMPONENT TEETH WHITENING, DESENSITIZATION AND REMINERALIZATION

BACKGROUND OF THE INVENTION

1. Field of the Invention

This invention relates generally to a single-use, disposable, multi-film delivery system for multi-component tooth whitening, desensitization and remineralization, which comprises an orally dissolvable film (ODF) and an undissolvable plastic or polymer film, the compositions on the films chemically activate to rapidly accelerate the tooth whitening, desensitizing and/or remineralizing effects. More particularly, the present invention relates to a first orally dissolvable film having a peroxide activation complex and desensitizing agents and/or remineralizing agents and/or anti-inflammatory agents and a polymer system for a controlled dissolution by interaction with the fluid or liquid contained in the whitening composition on the second undissolvable film, the said whitening composition also contains stabilizers and thickening agents. Even more particularly, the present invention relates to multi-film delivery systems that are thin, transparent, comfortable and inconspicuous when worn. This invention relates to methods of making such tooth whitening products, more particularly the methods of making the orally dissolvable film (ODF).

2. The Prior Art

A tooth is comprised of an inner dentin layer, and outer enamel layer coated with a protective layer called dental pellicle, which is a protein film that forms on the surface of enamel. The dental pellicle and the enamel can become extrinsically stained or discolored over time because the enamel layer of a tooth is porous, meaning that any substances such as coffee, red wine, tobacco, tea and foods that are rich in dark pigment can easily be absorbed within the pores, and accumulate on the enamel layer of the tooth and form a pellicle film over the teeth. Frequently eating these particular foods can cause stains and permanent discoloration of teeth.

There are several single-film based tooth whitening patches and strips, both in dissolvable and undissolvable forms, for home use available in the marketplace today. Their peroxygen concentrations range from 3-14% by weight. However, these compositions are considered to have a slow bleaching effect. These strips have the drawback of not chemically activating, and thus not efficiently whitening teeth and requiring users to wear for extended periods of time, usually 30 minutes or more. If the user chooses to wear for a short amount of time, the peroxygen contained on the whitening strips will not have enough time to breakdown into bleaching radicals and trigger the whitening effect. However, long wear times for whitening treatments often cause or are accompanied by sensitivity and/or demineralization of teeth, and hence separate desensitizing or remineralizing treatment is often needed afterward.

Peroxygen compounds have been used for many years in tooth whitening because the decomposition of these compounds produces free radicals that oxidize the colored organic molecules and inorganic compounds. Peroxygen compounds, for example, hydrogen peroxide, on their own are relatively weak oxidants under mild conditions: they can achieve some oxidations unaided, but for truly effective applications, it requires activation in one way or another.

The decomposition of hydrogen peroxide has been widely studied as a model reaction for its catalytic activity of various metal complexes and has also been studied as a catalase model. It has been known for about a century that the decomposition of $H_2O_2$ to $H_2O$ and $O_2$ is drastically accelerated by a few different factors. The rate of hydrogen peroxide decomposition increases with rising temperature, concentration and pH. Decomposition is catalyzed by various compounds, including most transition metals and their compounds (e.g. manganese dioxide, silver, and platinum). Certain metal ions, such as $Fe^{2+}$ or $Ti^{3+}$, can cause the decomposition to take a different path, with free radicals such as (HO.) and (HOO.) being formed. Non-metallic catalysts include potassium iodide, which reacts particularly rapidly. Hydrogen peroxide can also be decomposed biologically by enzyme catalase.

In one aspect, the present invention is based upon the discovery that when a peroxide containing component and peroxide activating agents such as transitional metal salts or complexes, enzymes, electrolytes, alkaline, and mixtures thereof, which are normally incompatible with each other and combined for the first time, result in catalytic decomposition of hydrogen peroxide, and releases active bleaching radicals that rapidly whiten teeth. The catalytic decomposition depends upon the concentration of $H_2O_2$, the concentration of the catalyst, temperature, and pH of the reacting solutions.

The multi-film delivery system also delivers additional benefits to consumers, yet provides convenience. Such additional benefits preferably include improved remineralization of the teeth, whitening of the teeth without pre-mixing or wasting of reagents and activators, better prevention of tooth sensitivity because anti-sensitivity ingredients can be separated from whitening compounds prior to usage and activated during application, and reduced wear time and enhanced level of comfort.

Illustrative of whitening strips containing peroxygen compounds for whitening teeth include U.S. Pat. Nos. 5,891,453, 7,785,572, 6,419,906, 6,893,629, 5,879,691, 6,949,240, 9,149,417 and 6,682,721.

U.S. Pat. No. 5,891,453 discloses a single-component transparent flexible strip material for delivering an adhesive tooth whitening substance. U.S. Pat. No. 5,879,691 discloses a single-component of transparent strip material having a flexural stiffness less than about 50 grams/centimeter and delivers a tooth whitening substance. The reasons for the apparent extreme similarities between U.S. Pat. Nos. 5,891, 453 and 5,879,691 are not clear. However, to those skilled in tooth whitening strip technology, it is apparent that the claims of U.S. Pat. No. 5,879,691 are covered by the claims of U.S. Pat. No. 5,891,453.

U.S. Pat. No. 7,785,572 discloses a single-component dry adhesive device comprising a matrix adhesive layer containing a peroxide teeth whitening agent and a hydrophilic glassy polymer as a base polymer, and a backing layer. U.S. Pat. Nos. 6,419,906 discloses a single-component anhydrous water hydratable ethylene oxide polymer matrix film containing a solid peroxide whitening agent which when applied to stained teeth is hydrated by saliva and whitens teeth. U.S. Pat. No. 6,949,240 discloses a single-component tooth whitening strip carrying a tooth whitening peroxide active having a concentration greater than about 7.5% by weight and peroxide density less than about 1.3 $mg/cm^2$. In comparison, the tooth whitening, desensitizing and remineralizing strip system described herein contains at least two film strips separate from each other prior to application.

U.S. Pat. No. 6,893,629 discloses a single-component, dissolvable, disintegrable film of flexible malleable polymer material having a tooth whitening substance dispersed within, when said film is adhered to the teeth, the film has a dissolution rate of about one hour during which to release its active tooth whitening substance. U.S. Pat. No. 9,149,417 discloses a single-component multi-layer dissolving tooth whitening strip comprises a solid dissolvable tooth contacting inner layer containing a tooth whitening active, and a dissolvable outer layer comprising a blend of polymers that dissolve after predetermined time and containing a tooth whitening active, and a bond forms between the tooth contacting inner layer and the outer layer by partially dissolving into each other during the film-casting process. U.S. Pat. No. 6,682,721 discloses a single-component multi-layer dry tooth whitening patch comprising a hydratable adhesive layer containing a stabilized peroxide tooth whitening agent and a peroxide-compatible hydrophilic glass polymer as a backing layer. In comparison, the multi-film tooth whitening, desensitizing and remineralizing strip system described herein contains a tooth contacting dissolvable adhesive film containing a peroxide activation complex and desensitizing agents and/or remineralizing agents and/or anti-inflammatory agents, and an undissolvable outer film strip containing a stabilized tooth whitening active and/or desensitizing agents and/or remineralizing agents and/or anti-inflammatory agents and fluid or liquid; the fluid or liquid in the outer film's composition dissolves the first tooth contacting orally dissolvable film and the first film's peroxide activation complex activates the peroxide compound on the second film and accelerate the tooth whitening action; the two said film strips are kept separate from each other until application.

It is well known that compliance in a therapeutic regimen has been shown to be directly related to the length of the therapy and the frequency of dosage. Hence, one object of this invention is to provide a system which can more rapidly whiten teeth by producing active bleaching species without undesirable long wear time (i.e.: for whitening strips with strong concentrations of 9.5% hydrogen peroxide or more: up to 2 hours a day, and requiring 7 days or more to show results; or for whitening strips with weaker concentrations of 7% hydrogen peroxide or less: the required frequency of usage of up to 28 days if worn for short period of 5 minutes per day). Another object of this invention is to provide with tooth whitening systems and compositions which can be used in the home by the consumer or can be used in the dental office. A further object of this invention is to provide desensitizing and/or remineralization effects during teeth whitening, with no additional wear time. Additionally, this invention can also be used to deliver effective in-situ remineralization by the reaction between phosphate source in the first orally dissolvable film and regeneration-source calcium salt on the second undissolvable film to generate hydroxyapatite, which reduces the likelihood of tooth sensitivity and tooth decay, and regenerates enamel.

DETAILED DESCRIPTION OF THE INVENTION

Definitions

The terms "film", "strip", "film strips" and "strips of film" are used interchangeably in this patent.

The terms "teeth whitening" and "bleaching" are used interchangeably in this patent.

Oral thin films or orally dissolvable films (ODFs) are films that contain film-forming polymers such as hydroxypropylmethyl cellulose (HPMC), hydroxyethyl cellulose (HEC), hydroxypropyl cellulose (HPC), pullulan, carboxymethyl cellulose (CMC), sodium carboxymethyl cellulose (Na-CMC), pectin, starch, gelatin, xanthan gum, polyvinylpyrrolidone (PVP), sodium alginate, and etc., alone or mixtures thereof.

Orally dissolvable film technology is a technology of making the said ODFs, which comprises incorporating the activating compound or composition and/or desensitizing agents and the additional ingredients within film-forming polymers by mixing and/or milling, and then forming films by modeling and/or casting or evaporating part of the liquid added.

A method of applying the multi-film delivery system for a multi-component tooth whitening substance comprises: placing the first orally dissolvable film on a surface of the tooth and then immediately or after a short time placing the second undissolvable film on top of the first orally dissolvable film.

All percentages, ratios and proportions herein are by weight, unless otherwise specified. All temperatures are in degrees Celsius (° C.) unless otherwise specified.

As used herein, "comprising" means that other steps and other ingredients which do not affect the end of result can be added. This term encompasses the terms "consisting of and "consisting essentially of.

Below is a brief description of the drawing:

FIG. 1 is a comparison of the solvent-casting and hot-melt extrusion methods.

FIG. 2 indicates the critical factors involved in ODF manufacture using the solvent-casting method.

Figure 6:
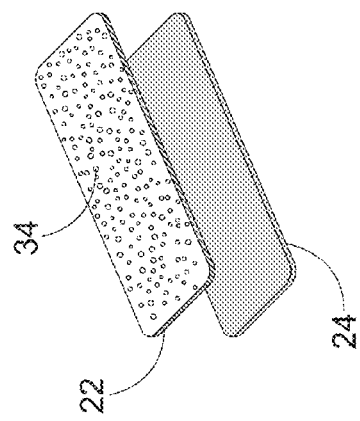
Figure 5:
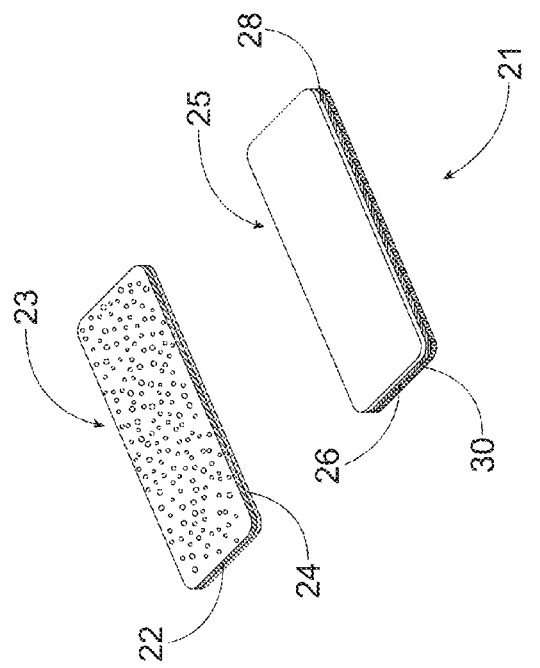
Figure 9:
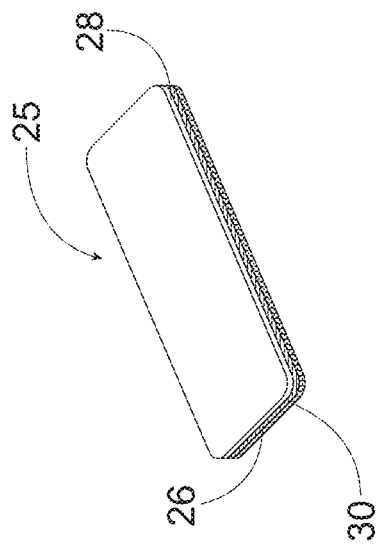
Figure 8:
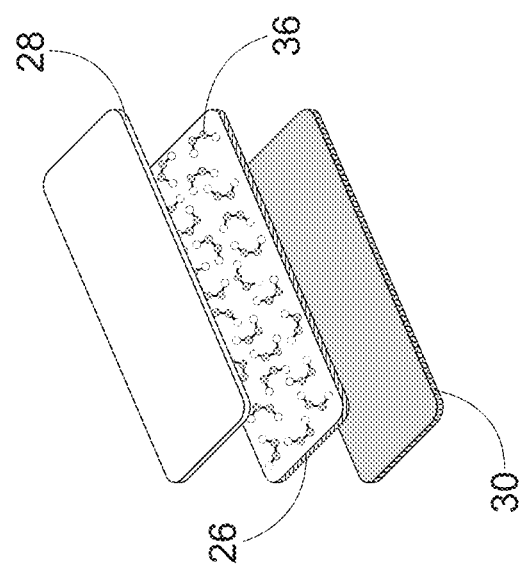

FIGS. 5, 6, 7, 8 and 9 show a preferred embodiment of the present invention, which is generally indicated as 21. Embodiment 21 represents a multi-film delivery system for multi-component teeth whitening, desensitization and remineralization. The first orally dissolvable film 23 of delivery system 21 has an orally dissolvable film 22 and a release liner 24, both are substantially flat, preferably with rounded corners; the second undissolvable film 25 of delivery system 21 has a strip of film material 30, which is substantially in the same shape as the first orally dissolvable film 22, and release liner 28 attached to strip of film material 30 by whitening substance 26. Whitening substance 26 is sandwiched in between release liner 28 and strip of film material 30. Preferably, peroxide activating compound 34 is evenly and uniformly dispersed throughout the orally dissolvable film 22, as shown in FIG. 6. The first orally dissolvable film 22 has sufficient flexibility and tensile strength to form a curved shape around a plurality of adjacent teeth; after the dissolvable film 22 hydrates by contact with either wearer's saliva or the fluid/liquid contained in the whitening substance 26 on the second undissolvable film 30, it becomes gelatinous and readily conformable to tooth surfaces and to the interproximal tooth spaces when it is applied. The strip of film material 30 carrying whitening substance 26 is applied to the first film 22 once release liner 28 is removed.

Figure 12:
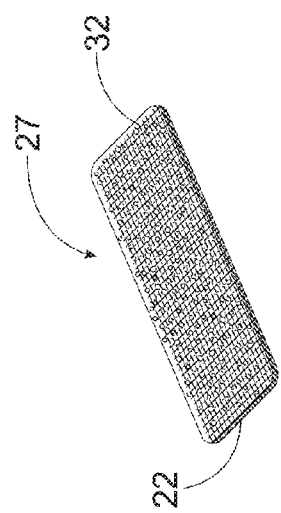
Figure 11:
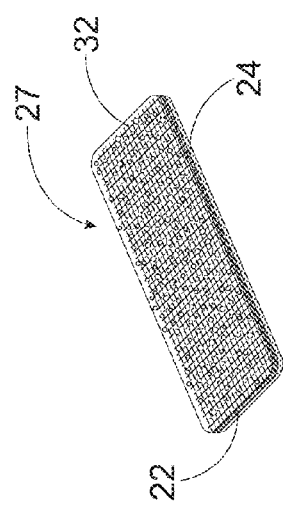
Figure 10:
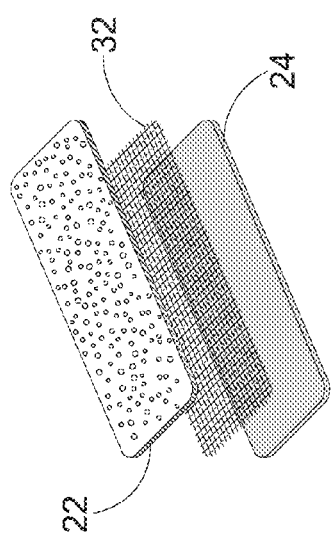

FIGS. 10, 11 and 12 show an alternative embodiment of the present invention, in which the first orally dissolvable film 22 incorporates or embeds a mesh layer 32 that provides the finished film with added flexibility, fracture resistance and tensile strength, wherein the mesh material is made of high density polyethylene (HDPE), low density polyethylene (LDPE), linear low density polyethylene (LLDPE), polypropylene (PP), polyvinyl acetate (PVA) or blends of these polymers; the resulting film 27 is essentially a partially orally dissolvable film (ODF) with the mesh layer 32 being the only remnant after application and dissolution.

Figure 13:
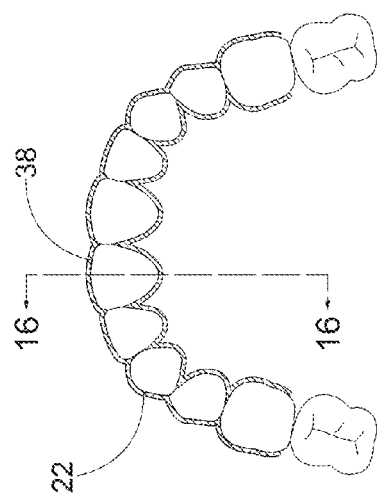

FIG. 13 shows first orally dissolvable film 22 and activating compound 34 of delivery system 21 of the present invention applied to both front and rear surfaces of a plurality of adjacent teeth 38, as well as to adjacent gum tissue 40 located by the front surfaces of the teeth. Adjacent gum tissue is herein defined as soft tissue surfaces surrounding the tooth structure including: papilla, marginal gingiva, gingival sulculus, inter dental gingiva, gingival gum structure on lingual and buccal surfaces up to and including muco-ginival junction and the pallet.

Figure 14:
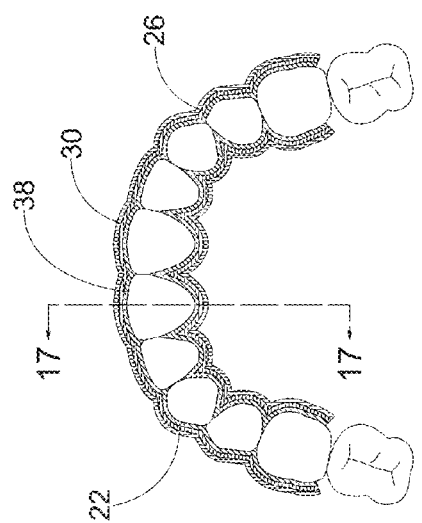

FIG. 14 shows second undissolvable film 30 and whitening substance 26 of delivery system 21 of the present invention applied on top of the first orally dissolvable film 22, with whitening substance 26 on the side of film material 30 facing the first orally dissolvable film 22.

Figure 15:
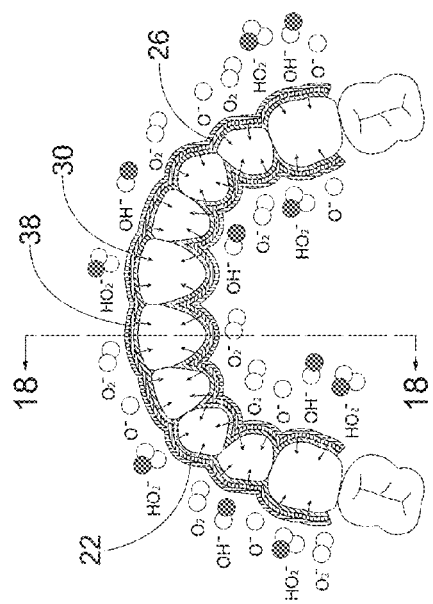

FIG. 15 shows the reaction between the peroxide activating compound 34 in the first film 22 and the peroxygen compound 36 in the whitening substance 26 on the second film 30 and accelerates the release of active bleaching radicals ($HO_2^-$, $OH^-$, $O_2^-$, $O^-$, $O_2$) for rapid whitening action. The dissolution of the first film 22 is controlled by either user's saliva or interaction of the fluid or liquid contained in the whitening substance 26 on the second film 30.

Figure 16:
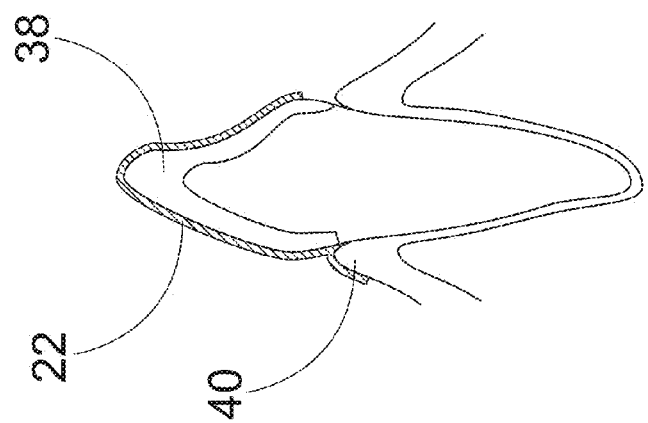

FIG. 16 is a cross-sectional side view taken along section line 16-16 of FIG. 13, showing the first orally dissolvable film 22 of the present invention conforming to both the tooth and the adjoining gum tissue and adhesively attached to both sides of the tooth by means of the orally dissolvable film 22 absorbing saliva and becoming gelatinous.

Figure 17:
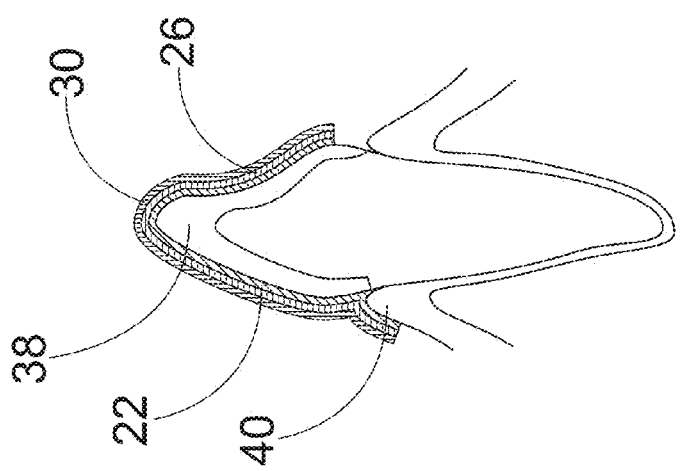

FIG. 17 is a cross-sectional side view taken along section line 17-17 of FIG. 14, showing the second undissolvable film 30 of the present invention applied on top of the first orally dissolvable film 22 while conforming to both the tooth and the adjoining gum tissue and adhesively attached to both sides of the tooth by means of the whitening substance 26 located between the first dissolvable film 22 and the undissolvable film 30.

Figure 18:
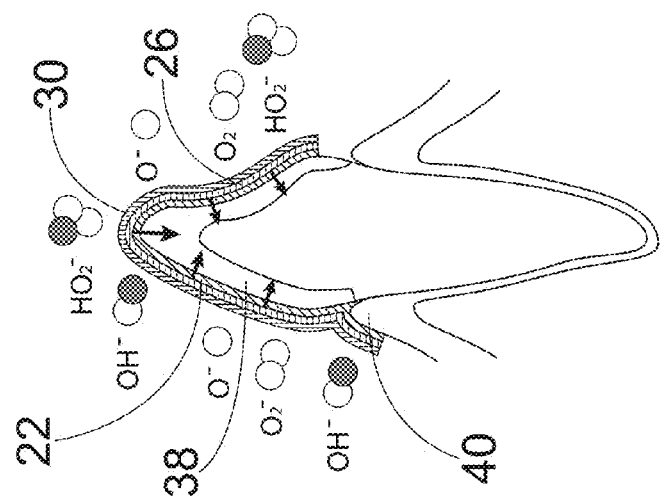

FIG. 18 is a cross-sectional side view taken along section line 18-18 of FIG. 15, showing the reaction between the peroxide activating compound 34 in the first film 22 and the peroxygen compound 36 on the second film 30 and accelerates the release of active bleaching radicals ($HO_2^-$, $OH^-$, $O_2^-$, $O^-$, $O_2$) for rapid whitening action.

FIGS. 19, 20 and 21 illustrate an alternative method of applying the multi-film delivery system 21 of the present invention: place the first dissolvable film 22 containing peroxide activating compound 34 on the second undissolvable film 30 carrying whitening substance 26 containing peroxygen compound 36, then place both films on a surface of the tooth, the peroxide activating compound 34 in the first film 22 and the peroxygen compound 36 on the second film 30 then reacts with each other and accelerates the release of active bleaching radicals ($HO_2^-$, $OH^-$, $O_2^-$, $O^-$, $O_2$) for rapid whitening action.

In one aspect, the present invention provides a multi-film delivery system for multi-component tooth whitening, desensitization and remineralization, wherein a first orally dissolvable film (ODF) 22 preloads at least one activating compound or composition 34 and/or desensitizing agents and/or remineralizing agents and/or anti-inflammatory agents, and a separate second undissolvable plastic or polymer film 30 comprises undissolvable, single or multi-layer thin strip of film 30 made of inert polymers such as polyethylene (PE), polypropylene (PP), polyvinyl chloride (PVC), and etc., and of which the whitening substance 26 is in gel form, containing a tooth whitening peroxygen compound 36, such as hydrogen peroxide, carbamide peroxide or sodium perborate; stabilizers, and thickening agents. When the two films applied together on teeth surfaces, the activating compound or composition 34 preloaded in the first film 22 activates the peroxygen compound 36 on the second film 30, and accelerates the release of active bleaching radicals for accelerated whitening action, and meanwhile, the compositions on the films desensitize and/or remineralize the teeth. This is illustrated by FIG. 15 and FIG. 18.

Preferably, the said orally dissolvable film (ODF) 22 is based on water soluble film-forming polymers, including but not limited to hydroxypropylmethyl cellulose (HPMC), hydroxyethyl cellulose (HEC), hydroxypropyl cellulose (HPC), pullulan, carboxymethyl cellulose (CMC), sodium carboxymethyl cellulose (Na-CMC), pectin, starch, gelatin, xanthan gum, polyvinylpyrrolidone (PVP), sodium alginate, chitosan derivatives, and etc., alone or mixtures thereof. The said ODF comprises mainly about 20% to 95% of the said water soluble polymers by weight of the total film weight.

Optionally, the said ODF comprises blends of the above-mentioned polymers with low and high molecular weight. Blends of different molecular weights offer additional advantages in the said ODF such as good mechanical properties for subsequent handling and converting into manufactured products. Preferably, such blends contain at least one type of polymer that has a molecular weight less than 20,000 and a second polymer or mixture of polymers having molecular weight greater than 50,000.

Optionally, the said ODF comprises less than 10% of water-insoluble film forming polymers, such as polyvinyl acetate (PVA), ethylene/vinyl copolymer (EVA), preferably having melt flow index from 2 to 200.

The average molecular weight of the said film forming polymers ranges from 5,000 to 500,000.

In other aspect, the said ODF comprises at least one peroxide activation compound/complex 34 and/or desensitizing agents and/or remineralizing agents and/or anti-inflammatory agents. Additional ingredients that are incorporated include plasticizers, sweetening and flavoring agents, coloring agents, saliva-stimulating agents, surfactants and thickening agents.

The peroxide activation compound/complex 34 is defined here as a transition metal salt or a transition metal complex consisting of a transition metal compound and an chelating agent, and/or pH-enhancing agents, and/or electrolytes, and/or bioactive enzymes and etc., alone or mixtures thereof, which is capable of activating the peroxygen compound in a manner that produces active bleaching radicals.

The amount of peroxide activation compound/complex 34 (such as transition metal compound/complex, and/or pH-enhancing agents, and/or electrolytes, and/or bioactive enzymes and etc., alone or mixtures thereof) present in the first dissolvable film 22 of the multi-component tooth whitening, desensitizing, remineralizing, and anti-inflammatory strip system of the present invention will vary depending upon the amount of peroxygen compound 36 incorporated in the second undissolvable film 30. For use by trained dental professionals in chairside procedures or dentist-monitored treatments, and the second undissolvable film 30 contains relatively high concentrations of a peroxygen compound, e.g. between about 9% to about 40% by weight, the amount of peroxide activation compound 34 incorporated in the first dissolvable film 22 will range between about 0.1% to about 10% by weight and preferably between about 0.2% to about 5% by weight. For take-home applications in which the concentration range of peroxygen compound 36 on the second undissolvable film is between about 0.1% to about 15% by weight, lower concentrations, e.g., between about 0.01% to about 5% by weight of the peroxide activation complex 34 is included in the first dissolvable film 22 and preferably about 0.02% to about 1% by weight of the activator is used.

Additionally, surfactants can be used to disperse the peroxide activation compound/complex and improve the diffusion of the free radicals and thus achieve effective whitening results while wearing the multi-film delivery system. Preferred polymeric surfactants include polyethylene glycol with molecular weight greater than 2000, polyoxyethylene/polyoxypropylene block copolymer, polyvinylpyrrolidone (PVP), polyvinyl alcohol and the like.

In other aspect, the first said ODF is substantially thin and comfortable when worn, wherein the said films typically have a thickness between 50 μm and 1 mm, and preferably have certain stretching strength or flexibility. The design can vary from single to multi-layer systems.

In addition, the present invention provides a technology of making the said ODFs, which is called orally dissolvable film technology. The said orally dissolvable film technology comprises incorporating the activating compound or composition and/or desensitizing agents and the additional ingredients within film-forming polymers by mixing and/or milling, and then forming films by modeling and/or casting or evaporating part of the liquid added.

Figures 1, 2:
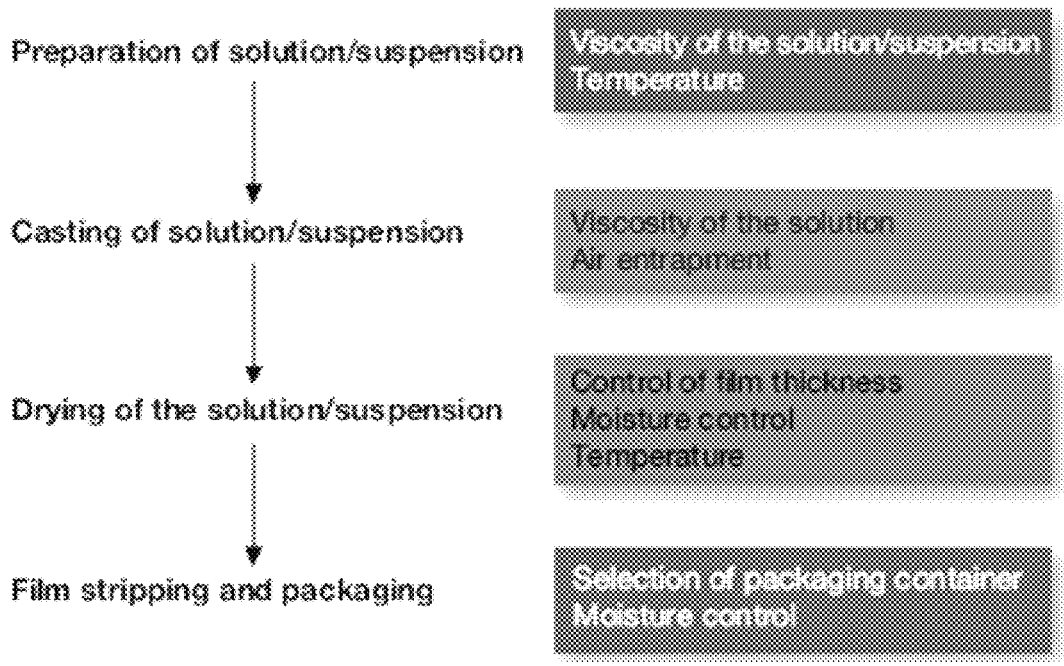

In one aspect, the first orally dissolvable film (ODF) 22 can be prepared by one or a combination of the following process: solvent casting, semisolid casting, hot-melt extrusion (HME), solid-dispersion extrusion, and rolling. The most commonly used methods of film manufacturing are solvent casting and HME. FIG. 1 is a comparison of the solvent-casting and hot-melt extrusion methods for manufacturing orally dissolvable films.

In other aspects, the ODF is preferably prepared using the solvent-casting method, whereby the water-soluble ingredients are dissolved to form a clear, viscous solution. The other ingredients are dissolved or dispersed homogeneously in a liquid dispersant. This mixture is then added to another aqueous, viscous solution. The entrapped air is removed by vacuum. Deaeration is necessary to obtain uniform film property and thickness. The resulting solution is cast as a film, allowed to dry, and cut into pieces to the desired size.

The properties of the film-forming polymers play a critical role in the selection of a suitable solvent. The physico-chemical properties of the film-forming polymers should be considered. These properties include compatibility of the film-forming polymers with other film-forming excipients, compatibility with solvents, the polymorphic nature of the film-forming polymers selected, and temperature sensitivity.

In a further aspect, the ODF is prepared using less than 20% by weight of the total film weight of liquids/solvents, such as water, alcohol, and etc., alone and the mixtures thereof. The solvents may be added while mixing in order to disperse the ingredients well. Preferably, part of the liquids added is to be evaporated while molding or casting.

FIG. 2 indicates crucial factors involved in manufacturing orally dissolvable films using the solvent-casting method.

Hot-melt extrusion (HME): HME is commonly used to prepare granules, sustained-release ingredients, and transdermal and transmucosal delivery systems. The HME process recently has gained popularity in the pharmaceutical industry. Based on knowledge from the plastics industry, formulators can extrude combinations of active ingredients, polymers, and plasticizers into various final forms to achieve desired release profiles. Processing films by this technique involves shaping a polymer into a film via the heating process rather than through the traditional solvent-casting method. In the HME process, the active ingredients and other excipients are mixed in a dry state, the heating process is started, and the molten mass is extruded out of the hot-melt extruder. The advantage of this process is the complete elimination of the solvent. The films are allowed to cool and are cut to the desired size. The high temperature used in the process makes it suitable for thermostable ingredients. Ingredients that are sensitive to temperature cannot be used in this process.

Figure 3:
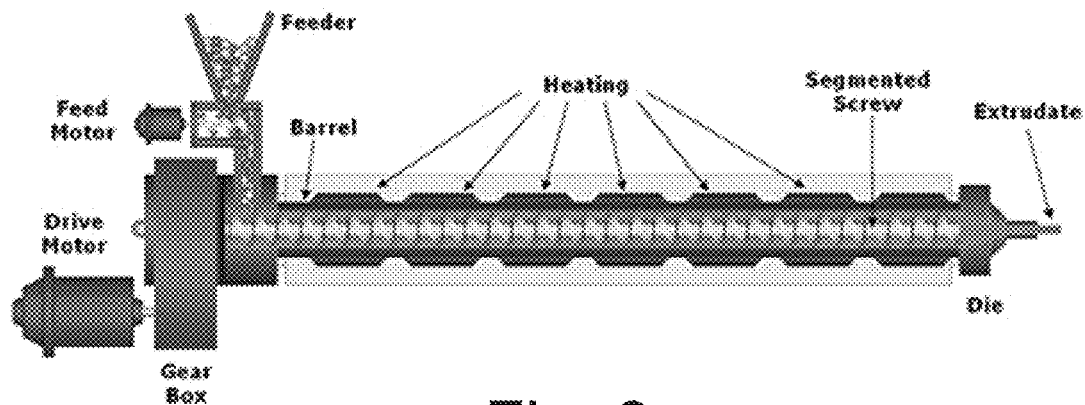
FIG. 3 shows the critical processes involved in ODF manufacture using the hot-melt extrusion (HME) method.

FIG. 3 shows the critical processes involved in ODF manufacture using the Hot-melt extrusion (HME) method.

Preferably, at least one plasticizer such as glycerin, propylene glycol, polyethylene glycol (PEG) 200, 400, 600, polymer PEGs, copolymer of polyethylene oxide and polypropylene oxide, and mixtures thereof, is used when making the said ODF. The amount of the plasticizers can vary from 0.1% to 40%, preferably, from 0.5% to 10% by weight.

Stability of the film and its mechanical properties are significantly affected by the presence of moisture. Another factor requiring strict control is temperature. Controlled temperature conditions are required for maintaining the viscosity of the solution and temperature sensitivity of the active ingredients. Specific types of equipment such as rollers are required for pouring the solution on an inert base. The clearance between the roller and the substrate determines the required thickness of the film. The final step, drying the film, removes the solvent and helps to obtain the finished product. Usually, glass, plastic, or Teflon plates are used as an inert base for film casting. The selection of the proper type of dryer is needed in the final step of drying. Manufacturing and packaging ODFs requires special precaution to be taken to control the effect of moisture.

Preferably, the said orally dissolvable film technologies are polymer films that may contain reagents or other active materials designed to erode or dissolve at predetermined rates when in contact with a biological fluid or other liquid. This is an efficient medium for stabilizing sensitive reagents, delivering therapeutic agents or dispersing pigments.

The vehicles used to prepare the individual films of the multi-component tooth whitening, desensitizing, remineralizing, and anti-inflammatory strip system of the present invention are entirely different. The first orally dissolvable film 22 is made of single or multi-layer film-forming polymers such as hydroxypropylmethyl cellulose (HPMC), hydroxypropyl cellulose (HPC), pullulan, carboxymethyl cellulose (CMC), pectin, starch, polyvinyl acetate (PVA), gelatin, and sodium alginate; with additional incorporated ingredients including plasticizers, sweetening and flavoring agents, coloring agents, saliva-stimulating agents, and thickening agents. The second undissolvable film 30 is made of single or multi-layer inert polymers such as polyethylene (PE), polypropylene (PP), nylon, polyvinyl chloride (PVC), and etc. The vehicle used to prepare the composition 26 on the second undissolvable film 30 includes water and/or a suitable humectant such as glycerin, propylene glycol, polyethylene glycol, or any suitable mixture thereof. Water is preferred as a humectant in the practice of the present invention.

Figure 4:
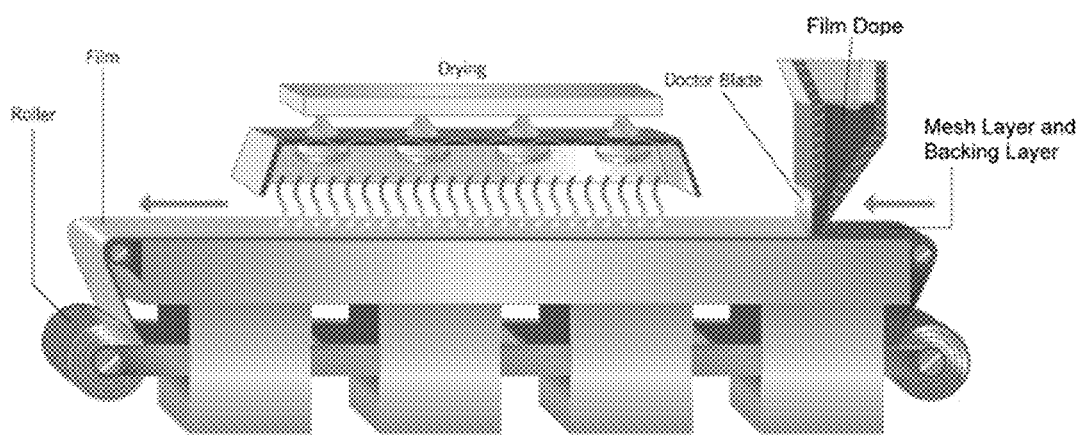
FIG. 4 illustrates an alternative process for ODF manufacturing embedding a mesh layer 32 and utilizing film rolling.
Figure 7:
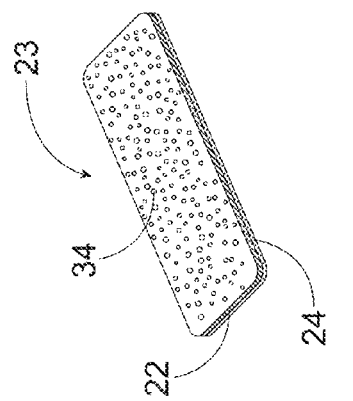

An alternative way of preparing the first orally dissolvable film 22 can incorporate or embed a mesh layer 32 that provides the finished film with added flexibility, fracture resistance and tensile strength, wherein the mesh material is made of high density polyethylene (HDPE), low density polyethylene (LDPE), linear low density polyethylene (LLDPE), polypropylene (PP), polyvinyl acetate (PVA) or blends of these polymers, and the said mesh material has an air porosity from 200 cfm to 2000 cfm, a thickness of from about 0.025 mm to about 0.25 mm, and a basis weight from 3.4 g/m$^2$ to 85 g/m$^2$; the resulting film 27 essentially becomes a partial orally dissolvable film (ODF) with the only remnant being the mesh layer 32 after application and dissolution. FIG. 4 illustrates an alternative process for ODF manufacturing embedding a mesh layer 32 and utilizing film rolling.

FIG. 4 illustrates an alternative process for ODF manufacturing involving a mesh layer 22 and rolling.

In one aspect, on the second undissolvable film 30, there is a whitening substance in gel form which contains a tooth whitening peroxygen compound, such as hydrogen peroxide or carbamide peroxide, stabilizers, thickening agents, etc.

Peroxygen compounds used in the compositions of the invention preferably include hydrogen peroxide, carbamide peroxide (urea peroxide), metal peroxides such as calcium peroxide, sodium peroxide, strontium peroxide, magnesium peroxide, and the salts of perbotate, persilicate perphosphate and percarbonate such as sodium perborate, potassium persilicate and sodium percarbonate. The most effective peroxygen compound for this invention is hydrogen peroxide and carbamide peroxide. The useful range of peroxygen compound is between about 0.1% to about 35% by weight. The preferred range is between about 1% to about 20% by weight. The amount of peroxygen compounds incorporated in the second undissolvable film 30 of the multi-film delivery system for multi-component teeth whitening, desensitization and remineralization of the present invention will vary dependent upon its intended use.

Preferably, peroxygen compounds are stabilized by adding into the whitening gel stabilizers, selected from the group of EDTA and its salt, potassium stannate, sodium stannate, etidronic acid, phosphoric acid, sodium pyrophosphate. Thickening agents are critical to obtain a viscous gel so that it can adhere onto the second film prior to application and adhere to both the second film and the first film while applying. The thickening agents are selected from crosslinked polyacrylic acid, polyvinylpyrrolidone (PVP), copolymer of polyethylene oxide and polypropylene oxide, and the mixture of thereof.

In another aspect, the two films are maintained separately until application to the teeth wherein the peroxide activation compound/complex 34 on the first orally dissolvable film 22 interacts with the peroxygen compound 36 on the second film 30 to accelerate the rapid release of active bleaching radicals from the peroxygen compound 36, such rapid release being highly effective for whitening teeth as illustrated in FIG. 15 and FIG. 18. The present invention offers the advantages that the premature breakdown of the peroxygen compound 36 is avoided, and the active bleaching radicals are generated quickly and in large quantities thereby facilitating shorter wear time, better efficacy and improved user comfort for the consumer as well as use by professionals, such as dentist performed chairside tooth whitening procedures.

In a further aspect, the present invention offers a method of applying the multi-film delivery system for a multi-component tooth whitening, desensitization or in-situ remineralization substance. As illustrated in FIG. 13 and FIG. 14 (also in FIG. 16 and FIG. 17), the method of application consists of:

a) placing the first orally dissolvable film 22 on a surface of the tooth, wait for a few seconds (between 1 second and 59 seconds) or until the film 22 absorbs saliva thus becoming gelatinous and activating its adhesive properties, then placing the second undissolvable film 30 on top of the first orally dissolvable film 22; or, b) placing the first orally dissolvable film 22 on a surface of the tooth, then immediately placing the second undissolvable film 30 on top of the first orally dissolvable film 22; or, c) placing the first dissolvable film 22 on the second undissolvable film 30, wait for a few seconds (between 1 second and 59 seconds) or until the first film 22 absorbs the fluid or liquid on the second film 30 thus becoming gelatinous and activating the peroxide on the second film 30, then placing both films on a surface of the tooth.

Benefits of the multi-film tooth whitening, desensitizing and remineralizing delivery system when compared to existing single-component whitening strip systems:

The contact of the first dissolvable film 22 and the second undissolvable film 30 instantly activates and catalyzes the decomposition of peroxygen compound 36 on the second film 30;

Greatly reduced wear time to achieve the same or better whitening, desensitization and remineralization result;

Separation of the whitening complex (active ingredient) 36 and the peroxide activation complex 34 improves the stability of the compositions and shelf-life;

Separation of the calcium complex and the phosphate complex allows the generation of precursors for in-situ hydroxyapatite formation on teeth;

Dry film format further improves reagent stability.

Below is a typical composition of ODF:

| Components | Concentration (%) |
|---|---|
| Active ingredient | 1-25 |
| Hydrophilic polymer | 40-50 |
| Plasticizer | 0-20 |
| Color, filler, flavor | 0-40 |

The following examples are further illustrative of the present invention, but it is understood that the invention is not limited thereto. All amounts and proportions referred to herein and the appended claims are by weight.

EXAMPLE 1

An example formulation of the first ODF is made according to the present invention, containing mixtures of Xanthan Gum, HPMC and PVA as film-forming polymers, transition metal salt, manganese gluconate as peroxide activating agent, PVP as surfactant, and etc. The film is prepared using the solvent-casting method. The solvent, ethanol is added to disperse the film-forming polymers and is evaporated afterwards.

| Composition ranges of various ingredients used in the first ODF | |
|---|---|
| Ingredient | (%) |
| DI water | 10 |
| Ethanol | 7 |
| Manganese Gluconate | 1.5 |
| PVP | 2 |
| PEG 8000 | 2 |
| Xanthan Gum | 16 |

Composition ranges of various ingredients used in the first ODF

| Ingredient | (%) |
|---|---|
| HPMC (high viscosity) | 18 |
| HPMC (low viscosity) | 18 |
| PVA | 2 |
| Potassium Nitrate | 2 |
| Nano-hydroxyapatite | 5 |
| Sucralose | 0.3 |
| Aloe vera | 0.6 |
| PEG 400 | 2 |
| Propylene Glycol | 13 |
| Flavorant | 0.6 |

EXAMPLE 2

Another example formulation of the first ODF is made according to the present invention, containing mixtures of PVP with low molecular weight of 3,000 and PVP with high molecular weight of 36,000, and PVA as film-forming polymers, transition metal salt, manganese gluconate as peroxide activating agent, PVP as surfactant, and etc. Propylene glycol was used as a liquid dispersant. The film is prepared using the hot-melt extrusion method.

Composition ranges of various ingredients used in the first ODF

| Ingredient | (%) |
|---|---|
| DI water | 5 |
| Propylene Glycol | 15 |
| Manganese Gluconate | 1.5 |
| PVP | 3 |
| PEG 2000 | 3 |
| PVP (36,000) | 10 |
| PVP (3,000) | 20 |
| PVP (60,000) | 23 |
| PVA | 10 |
| Potassium Nitrate | 1 |
| Nano-hydroxyapatite | 5 |
| Sucralose | 0.3 |
| Aloe vera | 0.6 |
| PEG 400 | 2 |
| Flavorant | 0.6 |

EXAMPLE 3

An example formulation of the first ODF is made according to the present invention, containing mixtures of Xanthan Gum, PVP with low molecular weight of 3,000 and PVP with high molecular weight of 36,000, PVA as film-forming polymers, transition metal salt, manganese gluconate as peroxide activating agent, and etc. The film is prepared using a combination of solvent casting method and hot-melt extrusion method. The solvent, ethanol, is added to disperse the film-forming polymers and is evaporated afterwards.

Composition ranges of various ingredients used in the first ODE

| Ingredient | (%) |
|---|---|
| DI water | 5 |
| Propylene Glycol | 10 |

Composition ranges of various ingredients used in the first ODE

| Ingredient | (%) |
|---|---|
| Manganese Gluconate | 1.5 |
| PVP | 4 |
| PEG 8000 | 2 |
| Xanthan Gum | 12 |
| PVP (3000) | 25 |
| PVP (36,000) | 25 |
| PVA | 6 |
| Potassium Nitrate | 1 |
| Nano-hydroxyapatite | 5 |
| Sucralose | 0.3 |
| Aloe vera | 0.6 |
| PEG 400 | 2 |
| Flavorant | 0.6 |

What is claimed is:

1. A multi-film delivery system for a multi-component tooth whitening, desensitization and/or remineralization composition, wherein the delivery system comprises:
    a. a first orally dissolvable film made of a liquid-soluble or liquid dispersible polymer system that preloads at least one activating compound or composition and/or desensitizing agents and/or remineralizing agents and/or anti-inflammatory agents; and
    b. a separate second undissolvable film containing a tooth whitening peroxygen compound, such as hydrogen peroxide or carbamide peroxide, which, when applied together on teeth surfaces, the activating compound or composition preloaded in the first film activates the peroxygen compound on the second film, and accelerates the release of active bleaching radicals for accelerated whitening action.

2. The first orally dissolvable film of claim 1, wherein the said orally dissolvable film (ODF) is based on water soluble film-forming polymers, including but not limited to hydroxypropylmethyl cellulose (HPMC), hydroxyethyl cellulose (HEC), hydroxypropyl cellulose (HPC), pullulan, carboxymethyl cellulose (CMC), sodium carboxymethyl cellulose (Na-CMC), pectin, starch, gelatin, xanthan gum, polyvinylpyrrolidone (PVP), sodium alginate, chitosan derivatives, alone or mixtures thereof, having an average molecular weight from 5,000 to 500,000.

3. The first orally dissolvable film of claim 1, wherein the said orally dissolvable film (ODF) comprises about 20% to 95% of water soluble film-forming polymers by weight of the total film weight.

4. The first orally dissolvable film of claim 1, wherein the said orally dissolvable film (ODF) is optionally containing non-water soluble polymers, such as polyvinyl acetate (PVA), ethylene/vinyl copolymer (EVA), preferably having melt flow index from 2 to 200.

5. The first orally dissolvable film of claim 1, wherein the said orally dissolvable film (ODF) comprises from 0.1% to 10% of non-water soluble polymers by weigh of the total film weight.

6. The first orally dissolvable film (ODF) of claim 1, wherein the said orally dissolvable film (ODF) contains at least one activating agent selected from transitional metal salts comprising ferric, manganese, copper, compound and/or complex; pH-enhancing agents, selected from sodium hydroxide, potassium hydroxide; ammonium hydroxide, triethynolamine, tris(hydroxymethyl)aminomethane; electrolytes, selected from alkaline salts; bioactive enzymes, alone or mixtures thereof.

7. The first orally dissolvable film (ODF) of claim 1 wherein the said orally dissolvable film (ODF) contains desensitizing agents selected from potassium nitrate, sodium citrate, calcium nitrate, alone or mixtures thereof and/or remineralizing agents, selected from nano-hydroxyapatite, nano-fluoroapatite, casein phosphopeptide-amorphous calcium phosphate, calcium phosphate (fluoride) nano-complex, bioactive glass, sodium monoflurophosphate, potassium monofluorophosphate, magnesium monofluorophosphate, acidulated fluorophosphate, amine fluoride, water-soluble salts of fluoride, comprising sodium fluoride, potassium fluoride, calcium fluoride, stannous fluoride, sodium fluorosilicate, bis-salicylato-bis-fluorotitanium (IV), ammonium fluorosilicate, calcium salt, phosphate salt, calcium salt/phosphate salt, calcium salt/ionic fluoride sources, zinc salt/phosphate salt), alone or mixtures thereof.

8. The first orally dissolvable film (ODF) of claim 1, wherein the said orally dissolvable film (ODF) contains sweetening agents, selected from sucralose, saccharin, xylitol; flavoring agents, chosen from the group consisting of citrus flavors, mint, chocolate, berries, which can be used both singularly and in suitable combinations; coloring agents, saliva-stimulating agents, surfactant, sweetening agents, plasticizers, and thickening agents.

9. The first orally dissolvable film (ODF) of claim 1, wherein the said film is substantially thin and comfortable when worn.

10. The first orally dissolvable film (ODF) of claim 1, wherein the said films typically have a thickness between 50 μm and 1 mm, yet flexible and stretchable; the design can vary from single to multi-layer systems.

11. The second undissolvable film of claim 1, wherein the said film comprises multi-layer but thin film strips, of which at least one layer of film strip is made of inert polymer selected from polyethylene (PE), polypropylene (PP), polyvinyl chloride (PVC), and of which the whitening substance is in gel form, containing a tooth whitening peroxygen compound, selected from hydrogen peroxide or carbamide peroxide; stabilizers, humectants, thickening agents.

12. The second undissolvable film of claim 1, wherein the said film is substantially thin and comfortable when worn.

13. The second undissolvable film of claim 1, wherein the said film typically has a thickness between 50 μm and 500 μm.

14. A technology of making the said ODFs, which is called orally dissolvable film technology, comprises incorporating peroxide activating compound or composition and/or desensitizing agents and/or remineralizing agents and the additional ingredients within film-forming polymers by solvent casting, semisolid casting, hot-melt extrusion (HME), solid-dispersion extrusion, or rolling, and then forming films by casting or evaporating part of the liquid added.

15. The orally dissolvable film technology according to claim 14, wherein less than 20% by weight of the total film weight of liquids/solvents, selected from water, alcohol, alone and the mixtures thereof may be added while mixing in order to disperse the ingredients well; part of the liquids added is to be evaporated while drying or casting.

16. The orally dissolvable film technology according to claim 14, wherein film-forming polymers selected from hydroxypropylmethyl cellulose (HPMC), hydroxyethyl cellulose (HEC), hydroxypropyl cellulose (HPC), pullulan, carboxymethyl cellulose (CMC), sodium carboxymethyl cellulose (Na-CMC), pectin, starch, gelatin, xanthan gum, polyvinypyrididone (PVP), sodium alginate, chitosan derivatives, polyvinyl acetate (PVA), ethylene/vinyl copolymer (EVA), and mixtures thereof, are used as a matrix of the ODFs.

17. The orally dissolvable film technology according to claim 14, wherein the said ODF comprises about 20% to 95% of water soluble polymers and/or about 0.1% to 10% of water-insoluble polymers, by weight of the total film weight.

18. The first orally dissolvable film of claim 14, wherein the said orally dissolvable film (ODF) is made by various processes, including but not limited to solvent casting, semisolid casting, hot-melt extrusion (HME), solid-dispersion extrusion, or rolling, and the process can optionally incorporate or embed a mesh layer that provides the finished film with added flexibility, fracture resistance and tensile strength, wherein the mesh material is made of high density polyethylene (HDPE), low density polyethylene (LDPE), linear low density polyethylene (LLDPE), polypropylene (PP), polyvinyl acetate (PVA) or blends of these polymers, and the said mesh material has an air porosity from 200 cfm to 2000 cfm, a thickness of from about 0.025 mm to about 0.25 mm, and a basis weight from 3.4 $g/m^2$ to 85 $g/m^2$, the resulting film is essentially a partial orally dissolvable film (partial ODF).

19. The orally dissolvable film technology according to claim 14, wherein at least one plasticizer selected from glycerin, propylene glycol, polyethylene glycol (PEG) 200, 400, 600, polymer PEGs, copolymer of polyethylene oxide, polypropylene oxide, diethyl phthalate, triethyl citrate, tributyl citrate, and mixtures thereof, is used to increase the workability, spreadability and flexibility of the ODF.

20. The orally dissolvable film technology according to claim 14, wherein the said ODF comprises the activating compound or composition containing transitional metal salts selected from ferric, manganese, copper, compound and/or complex; pH-enhancing agents, selected from sodium hydroxide, potassium hydroxide; ammonium hydroxide, triethynolamine, tris(hydroxymethyl)aminomethane; electrolytes, such as alkaline salts; bioactive enzymes, and the mixtures thereof.

21. The orally dissolvable film technology according to claim 14, wherein the said ODF comprises desensitizing agents selected from potassium nitrate, sodium citrate, calcium nitrate, alone or mixtures thereof and/or remineralizing agents, selected from nano-hydroxyapatite, nano-fluoroapatite, casein phosphopeptide-amorphous calcium phosphate, calcium phosphate (fluoride) nano-complex, bioactive glass, alone or mixtures thereof and/or anti-inflammatory agents, selected from Bis-phenols (e.g.: triclosan), Cyclines, Aloe vera, Menthol, carboxymethyl cellulose (CMC)-probiotic-OTF, *Sambucus nigra, Allium sativum, Camellia sinensis*, alone or mixtures thereof.

22. The orally dissolvable film technology according to claim 14, wherein the said ODF comprises additional ingredients that are incorporated including sweetening and flavoring agents, coloring agents, saliva-stimulating agents, thickening agents.

23. A method of applying the multi-film delivery system for a multi-component tooth whitening, desensitization, and remineralization substance comprises:
   a. placing the first orally dissolvable film on a surface of the tooth, wait for a few seconds (between 1 second and 59 seconds) or until the film absorbs saliva thus becoming gelatinous and activating its adhesive properties, then place the second undissolvable film on top of the first orally dissolvable film; or, b. placing the first orally dissolvable film on a surface of the tooth, then immediately place the second undissolvable film on top of the first orally dissolvable film; or, c. placing the first dissolvable film on the second undissolvable film, then place both films on a surface of the tooth.

24. The method according to claim 23, wherein the said first orally dissolvable film placed on a surface of the tooth immediately hydrates and thereby becomes gelatinous upon contact with saliva, and initiates its adhesiveness.

25. The method according to claim 23, wherein the activating substance on the said first orally dissolvable film reacts with the tooth whitening peroxygen compound on the second undissolvable film and accelerates the release of active bleaching radicals for rapid whitening action.

26. The method according to claim 23, wherein the dissolution of the said first orally dissolvable film of peroxide activation complex could be controlled by interaction with the fluid or liquid contained in the composition on the second undissolvable film.

\* \* \* \* \*